United States Patent [19]

Lancaster

[11] 4,185,964
[45] Jan. 29, 1980

[54] LYSING REAGENT

[75] Inventor: Robert G. Lancaster, Baltimore, Md.

[73] Assignee: Central Laboratories of Associated Maryland Pathologists, Ltd., Timonium, Md.

[21] Appl. No.: 766,731

[22] Filed: Feb. 8, 1977

[51] Int. Cl.² ............................................. G01N 33/16
[52] U.S. Cl. ................................. 23/230 B; 252/408; 424/11
[58] Field of Search ...................... 23/230 B; 252/408; 424/11

[56] References Cited

U.S. PATENT DOCUMENTS

| | | | |
|---|---|---|---|
| 3,874,851 | 4/1975 | Wilkins | 23/230 B |
| 3,874,852 | 4/1975 | Hamill | 23/230 B |
| 3,964,865 | 6/1976 | Das | 23/230 B |
| 3,977,995 | 8/1976 | Louderback | 23/230 B X |
| 4,013,417 | 3/1977 | Raffaele | 23/230 B X |
| 4,030,888 | 6/1977 | Yamamoto | 23/230 B X |
| 4,040,785 | 8/1977 | Kim | 23/230 B |

OTHER PUBLICATIONS

Chemical Abstracts, 70: 1593c (1969).

*Primary Examiner*—Sidney Marantz
*Attorney, Agent, or Firm*—Irons and Sears

[57] ABSTRACT

Azide-free blood diluents and cyanide ion-free erythrocyte lysing reagents which are particularly advantageous for use with Coulter scanning devices. The lysing reagent comprises (1) a water-soluble quaternary ammonium salt of the formula $R_1N(R_2)_3X$ wherein $R_1$ is a 12–20 C alkyl, each $R_2$ is the same or different and is lower alkyl or lower hydroxyalkyl and X is an anion, and (2) a minor amount of a water-soluble polycarboxylic acid.

22 Claims, No Drawings

LYSING REAGENT

This invention relates to blood diluents, lysing reagents, and methods for using the lysing reagents in the in vitro analysis of blood.

In common medical diagnosis practice, a blood sample from a patient is analyzed to determine, for instance, blood type, the concentration and size of red blood cells (erythrocytes), the concentration of white blood cells (leukocytes), and the concentration of hemoglobin. This information concerning the patient's blood properties may be of significant assistance to the physician in making a diagnosis. Devices are presently available which automatically make several determinations on a blood sample, thereby reducing human analytical efforts and chances of human error. Moreover, these devices also can rapidly process a blood sample, thereby providing the physician with prompt medical information. Exemplary of such devices are Coulter scanning devices which can automatically process blood samples to determine various characteristics of blood. U.S. Pat. No. 3,549,994, herein incorporated by reference, discloses a type of Coulter scanning device. These scanners measure the electroconductivity of a sample passing through an orifice, thus when a blood cell in an electrolytic medium passes through the orifice, a change in electroconductivity due to the different electroconductivity of the cell in the sample, is noted. The change in electroconductivity can not only record the presence of a cell, but also the degree of change in electroconductivity may also be indicative of the volume of the cell. These devices are often capable of determining the hemoglobin concentration in the blood by photocolorimetric means. For instance, the erythrocytes may be lysed, releasing hemoglobin which reacts, or complexes, with a reagent to form a chromogen. The light transmittance of the sample is then measured to determine the relative concentration of hemoglobin. With the stomatolysing of erythrocytes, the white blood cell count can be determined by the scanning device. By determining the red blood cell count and volume, the hemoglobin concentration, and the white blood cell count, various properties of the blood sample can be determined directly or by interrelation of two or more of these determinations. Blood properties which can be determined include, for instance, the red blood cell count (RBC), the hematocrit (HCT), the hemoglobin (HGB), the mean corpuscular volume (MCV), the mean corpuscular hemoglobin (MCH), the mean corpuscular hemoglobin concentration (MCHC), and the white blood cell count (WBC).

In analyzing blood, either using a Coulter scanning device or other analytical methods including manual microscopic evaluations, it is often necessary to dilute the blood sample due to the large concentration of cells in blood. In order to dilute the blood for clinical analysis but also obtain meaningful results therefrom, it is essential that the diluent not adversely affect the chemical and physical integrity of the blood corpuscles during the analysis. For instance, if the blood diluent is not isotonic and osmotically balanced with respect to the blood, the blood cells may shrink or expand. Moreover, the diluent should not adversely affect or interfere with the blood analysis or analyses, e.g., by affecting the resistance of blood cells to lysing or interfering with forming hemoglobin chromogens. The diluent should be free from particles which may interface with analyses of the blood. While the diluent may be filtered to remove particles larger than, for instance, about 0.2 micron in diameter at the time of its manufacture, the diluent may be susceptible to the support of microorganism growth after the manufacture and packaging of the diluent. The presence of microorganism growth may result in inaccurate and non-reproducible results in analyses such as those conducted by Coulter scanning devices.

It has been proposed to include an antimicrobic, or bacteriostatic, agent in blood diluents to retard the growth of microorganisms. The antimicrobic agent, however, must not adversely affect the blood cells or adversely affect or interfere with the analyses. If the antimicrobic agent affects the cell size by expanding the volume of the cell or shrinking the volume of the cell (crenation), the cell volume, and possibly cell count, analyses may be incorrect. Moreover, the antimicrobic agent may react or interfere with the reaction of a reagent to form a hemoglobin chromogen. Thus, although antimicrobic agents as preservatives for blood diluents are desirable, caution must be observed in their selection and use.

An antimicrobic agent which has been employed for many years in blood diluents is sodium azide. Although sodium azide generally does not unduly adversely affect a blood sample or interfere with the analyses of blood, e.g., using Coulter scanning devices, its use has been met with significant problems. Sodium azide is highly toxic, and aqueous solutions of sodium azide and vapors of hydrozoic acid therefrom may be potentially harmful to laboratory workers exposed to them. The disposal of sodium azide through, e.g., copper or lead-containing plumbing systems may result in the formation of heavy metal azides and their build-up over extended periods of time. Moreover, sodium azide is explosive when heated or shocked. Despite the need for alternatives to sodium azide as an antimicrobic agent in blood diluents, few alternatives have been proposed. Furthermore, the presence of sodium azide has been found to influence the formation of cyanmethemoglobin, a chromogen formed for determining hemoglobin in a blood sample. For instance, without sodium azide in the diluent, the hemoglobin as determined photometrically may be significantly different than that with the azide present. An alternative to the use of sodium azide which has been proposed is 2-phenoxyethanol as disclosed in U.S. Pat. No. 3,962,125, and sodium fluoride is essentially included in the proposed diluent to enhance hemoglobin chromogen formation.

When conducting a plurality of analyses on a blood sample including hemoglobin analysis, often the blood sample is diluted and then a lysing reagent is added for erythrocytolysis. The lysing reagent may also contain a substance which reacts or complexes with hemoglobin to form chromogens for spectrophotometric (hemoglobinometric) analysis wherein the optical density of the sample is directly proportional to the hemoglobin concentration. The lysing reagent should, therefore, not interfere with the formation of hemoglobin chromogens. Advantageously, the lysing reagent does not adversely affect the leukocytes which, due to the destruction of the erythrocytes, can be selectively measured, e.g., using Coulter scanning devices. The ratio of erythrocytes to leukocytes in blood is frequently in the vicinity of 1000:1, and thus, the erythrocytes must be quickly and efficiently lysed to prevent interference with leukocyte counting and provide reliable and reproducible hemoglobin concentration analyses. Moreover, the lysing reagent should not cause the formation of precipitates or large fragments from the lysed cells which would result in erroneous leukocyte counts.

The standard method for determining hemoglobin involves the use of Drabkin's reagent which contains potassium ferricyanide, potassium cyanide and sodium bicarbonate. The potassium ferricyanide is reduced to the ferrocyanide in the presence of hemoglobin which in turn is oxidized to methemoglobin. Methemoglobin reacts with the cyanide ion to form cyanmethemoglobin which is a relatively stable chromogen. Drabkin's reagent, however, has been found to be unsatisfactory since it is unstable upon exposure to freezing temperatures. Moreover, quaternary ammonium salts which have been found to be highly advantageous lysing agents and produce essentially instantaneous destruction of erythrocytes, may complex with the ferricyanide ion to form insoluble substances. A precipitate, no matter how insignificant, can falsely raise the leukocyte count as determined by Coulter scanning devices, and may adversely affect the photometric hemoglobin determination. In U.S. Pat. No. 3,874,852, it is proposed that a ferricyanide ion-free lysing reagent having a quaternary ammonium salt lysing agent be employed with potassium cyanide being provided as a reactant to form the hemoglobin chromogen. However, potassium cyanide is highly toxic and may be injurious to laboratory workers being exposed thereto. Accordingly, an alternative is sought to the use of highly toxic cyanides in lysing reagents for hemoglobin determinations, and desirably, the alternative would enable the use of quaternary ammonium salts as the lysing agents.

By my invention there is provided a diluent which is suitable for diluting blood for analyses of the blood and the physical and chemical integrity of the blood cells can be maintained. The diluent of my invention is essentially azide-free yet the diluent exhibits antimicrobic activity. The diluent is not deleterious to conducting various analyses of the blood nor does it provide significant toxicity risks to laboratory workers or problems in its disposal. The diluent of my invention is electrolytic, and can be essentially osmotically balanced to provide cell volume stability. The diluent of my invention can be employed for diluting blood samples for various blood cell and hemoglobin analyses such as those performed by automatic electronic particle analysis devices, e.g., Coulter scanning devices, and can be substantially compatible with existing calibration of Coulter scanning devices utilizing conventional azide-containing diluents.

In accordance with my invention, the blood diluent is an aqueous solution having a minor amount of at least one alkali or alkaline earth metal salt sufficient to provide an electrolytic solution having a pH and osmolality compatible with the blood cells, and a minor amount of a tri-substituted nitromethane antimicrobic agent sufficient to retard the growth of microorganisms in the diluent. Preferably, the substituents of the nitromethane are lower alkyl or lower hydroxyalkyl. The alkali and alkaline earth metal salts may include, for instance, the chloride, dihydrogen phosphate, monohydrogen phosphate, and phosphate salts. Generally, suitable diluents have a major amount of water, a pH of about 7 to 8, and an osmolality of about 300 to 380 milliosmoles per kilogram of diluent.

In another aspect, my invention is directed to lysing reagents for use in blood analyses which are stable and rapidly destroy erythrocytes. The lysing reagents of my invention also react, or complex, with hemoglobin to form chromogens having sufficient stability to permit the spectrophotometric determination of hemoglobin. Advantageously, the spectrophotometric determinations can be made employing existing equipment such as used to detect cyanmethemoglobin at a wavelength of about 500 to 580, e.g., about 525 or 540, nanometers with the use of substantially the same calibration. The lysing agent of my invention is an aqueous solution of a quaternary ammonium salt which is capable of forming chromogens with hemoglobin and a water-soluble polycarboxylic acid or salt in an amount sufficient to inhibit leukocytolysis. The lysing agent generally contains a major amount of water and is essentially cyanide ion-free (including ferricyanide ion-free), and thus does not provide undue toxicity risks to laboratory workers and others who may be exposed to the lysing agent. The chromogens which are formed provide an optical density of the resulting solutions which is proportional to the hemoglobin content. Moreover, the analytical results obtained when using the lysing reagents of this invention are highly reproducible.

In further detail, the blood diluent of my invention comprises, as the antimicrobic agent, a tri-substituted nitromethane having the formula

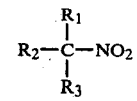

wherein $R_1$, $R_2$ and $R_3$ may be the same or different and may be lower alkyl or lower hydroxyalkyl, and preferably at least two of $R_1$, $R_2$ and $R_3$ are lower hydroxyalkyl. The lower alkyl and lower hydroxyalkyl groups preferably contain 1 to about 6, more preferably 1 to about 3, carbon atoms. Exemplary of the tri-substituted nitromethanes are tris(hydroxymethyl)nitromethane, 2-methyl-2-nitro-1,3-propanediol, 2-ethyl-2-nitro-1,3-propanediol and the like. The tri-substituted nitromethanes are provided in the solution in an amount sufficient to retard the growth of microorganisms. Often the amount of tri-substituted nitromethane employed is sufficient to provide an aqueous solution having a storage stability of at least about 1 year under ambient conditions. Frequently, the tri-substituted nitromethane is provided in an amount of at least about 50, preferably at least about 100, milligrams per liter of blood diluent, e.g., about 0.1 to 1 gram per liter.

The blood diluent contains at least one water-soluble alkali or alkaline earth metal salt to provide an electrolytic solution. The alkali or alkaline earth metal salt solution is substantially isotonic and osmotically balanced, i.e., the diluent is preferably buffered and has an osmolality compatible with blood such that the blood cells do not burst and are not unacceptably altered in volume. The diluent is buffered to provide a pH of about 7 to 8, preferably to a pH of about 7.2 to 7.6. Suitable buffering agents to provide pH levels in the desired range include the alkali and alkaline earth metal buffers such as the hydrogen phosphates, e.g., monobasic sodium phosphate, monobasic potassium phosphate, dibasic sodium phosphate, dibasic potassium phosphate, and mixtures thereof. For instance, a mixture of about 1.6 parts by weight monobasic potassium phosphate per 10 parts by weight dibasic potassium phosphate provides a buffer at a pH of about 7.4. The buffer is employed in a minor amount sufficient to provide the desired pH of the diluent, and frequently may be at least about 0.1, preferably at least about 0.5, grams per liter. The buffer may be provided in amounts up to about 20 or more grams per liter; however, such high concentrations of buffer which result in buffer remaining undissolved in the diluent are generally not employed in order to avoid the presence of undissolved solids which may affect blood analyses.

The buffer may influence the osmolality of the diluent; however, frequently an additional water-soluble alkali or alkaline earth salt is employed in an amount sufficient to provide a diluent having a suitable osmolality for blood analyses, e.g., about 300 to 380 milliosmoles per kilogram of diluent, more frequently about 320 to 340 milliosmoles per kilogram of diluent. Heretofore, the osmolality of diluents commonly employed for blood analyses, especially analyses by Coulter scanning devices, has been about 330 milliosmoles per kilogram of diluent. This osmolality level is slightly higher than that generally observed in blood plasma, and thus the red blood cells often swell slightly; however, since diluents having essentially the same osmolality can be employed, the results are substantially uniform and thus may be meaningful. Accordingly, by my invention the diluent may have an osmolality essentially the same as existing diluents to obviate the necessity of recalibrating existing equipment. The alkali or alkaline earth salts which may be employed include the alkali metal halide salts, e.g., halides having an atomic number of 9 to 35, such as sodium chloride, potassium chloride, sodium fluoride, potassium fluoride, and mixtures thereof. Frequently, the amount of alkali or alkaline earth salt which is employed in the diluent is at least about 1, preferably at least about 2, grams per liter, and often the desired osmolality is obtained employing no more than about 20 or 30 or more grams per liter. The salt is desirably essentially completely dissolved in the diluent to avoid the presence of undissolved solids.

The water employed to prepare the aqueous diluent is preferably sufficiently deionized that it has a resistance greater than one megohm per centimeter. The diluent may contain other conventional additives such as anticoagulants to abate agglutination of red blood cells, non-ionic surfactants, and the like. After admixing the components to form the diluent, the diluent is advantageously filtered to remove any solid particles which may result from, e.g., dust or contaminants, undissolved impurities in the components, incomplete solution of one or more components, and the like. The filter may have a pore size less than about one, preferably about 0.1 to 0.5, micron. The diluent may be stored in any suitable container, e.g., glass or plastic, sealed containers.

An example of a blood diluent of my invention is as follows with the specific example hereafter being referred to as blood diluent L:

| Component | grams per liter | |
|---|---|---|
| | Preferred | Specific |
| Tris(hydroxymethyl) nitromethane | 0.1 to 1 | 0.2 |
| Monobasic potassium phosphate | 0 to 5* | 0.4 |
| Dibasic potassium phosphate | 0 to 10* | 2.56 |
| Sodium chloride | 2 to 20 | 8.72 |

| Component | grams per liter | |
|---|---|---|
| | Preferred | Specific |
| Water | | quantity to make one liter. |

*at least one of monobasic potassium phosphate and dibasic potassium phosphate is present.

The phosphate salts are anhydrous technical or food grade, the sodium chloride is laboratory grade, i.e., does not contain the relatively insoluble anticaking agents typically found in table salt, and the water is deionized to provide a resistance greater than one megohm per centimeter. The diluent L is analyzed to have an osmolality of 330±5 milliosmoles per kilogram and a pH of 7.4±0.5. The background noise is about 25 as measured on a Coulter Model F scanning device obtainable from Coulter Electronics, Inc., of Hialeah, Florida, and having an aperture of 8, a threshhold of 10, an attenuation of 1, and 100 micron orifice.

The diluent is analyzed for integrity employing standard culture methods, i.e., by inoculating sterile, nutrient media with the diluent and incubating the inoculated media. After repeated openings and closings of a container containing the diluent over a period of one year, no microorganism growth in the culture media is observed when inoculated with the diluent and thus the diluent apparently remains sterile. Without the antimicrobic component, after two weeks, microorganism growth is observed in culture media inoculated with the diluent not containing the antimicrobic component. The diluent of my invention retains its performance characteristics for at least one year.

The lysing reagent of my invention is an aqueous solution containing a minor amount of a water-soluble quaternary ammonium salt which stromatolyses erythrocytes and forms chromogens with hemoglobin. The aqueous solution contains a major amount of water and is essentially free from cyanide ions, including complex cyanide anions such as ferricyanide. The quaternary ammonium salt may be of the formula $R_1 N(R_2)_3 X$ wherein $R_1$ and $R_2$ are aliphatic hydrocarbyl, and preferably $R_1$ is aliphatic hydrocarbyl, e.g. alkyl, of about 12 to 20, e.g., about 14 to 18, carbon atoms and each $R_2$ is the same or different and is lower alkyl or lower hydroxyalkyl, e.g., of 1 to about 6, preferably 1 to about 3, carbon atoms. The letter X designates an anion and may, for instance, be a halide such as chloride or bromide, sulfate, phosphate, nitrate, or the like anion. Exemplary of the quaternary ammonium salts which may be employed are cetyltrimethyl ammonium bromide, trimethyltetradecyl ammonium chloride, cetylethyldimethyl ammonium bromide, and the like. The amount of quaternary ammonium salt employed is sufficient to cause erythrocytolysis. Advantageously, the quaternary ammonium salt is provided in such concentrations that erythrocytolysis proceeds rapidly, e.g., essentially complete erythrocytolysis occurs in about 5 seconds or less. The quaternary ammonium salt is usually provided in excess of the amount required on a stoichiometric amount to form chromogens with hemoglobin. Frequently, the amount of quaternary ammonium salt employed is at least about 5, preferably at least about 10, grams per liter of lysing reagent such that the concentration of the quaternary ammonium salt in admixture with blood for lysing is at least about 0.5, preferably at least about 1, gram per liter. Generally, the quaternary ammonium salt comprises no more than about 50 or 100 grams per liter of the lysing reagent.

Often quaternary ammonium salts may also cause some leukocytolysis. Accordingly, a polycarboxylic acid or salt may be incorporated into the solution in a minor amount sufficient to inhibit leukocytolysis. The polycarboxylic acid generally has up to about 8 carbon atoms, often has 2 to about 4 carboxylic groups, and frequently contains at least one hydroxyl group. The polycarboxylic acid or salt is water-soluble, and generally the salt comprises alkali metal salt to enhance water solubility. Suitable polycarboxylic acids and salts include citric acid, sodium citrate, potassium citrate, tartaric acid, sodium tartrate, potassium tartrate, sodium potassium tartrate, sodium hydrogen tartrate, potassium hydrogen tartrate, and the like. The polycarboxylic acid or salt may comprise at least about 1, and say, up to about 50 to 100 or more grams per liter of lysing reagent; however, preferably the concentration of polycarboxylic acid is not so great that undissolved solids are contained in the lysing reagent. Often, the polycarboxylic acid or salt comprises about 5 to 50 grams per liter of the solution.

In scanning devices wherein blood samples are passed through an orifice, especially blood samples after lysing of erythrocytes, deposits may tend to form adjacent the orifice. A minor amount of water-miscible, organic solvent, e.g., comprising a lower alkanol, say, of 1 to about 4, preferably 1 to 3, carbon atoms may be employed in the lysing reagent to retard formation of these deposits. Frequently, the lysing reagent may comprise at least about 0.5 volume percent of the solvent, e.g., about 1 to 10 volume percent of the solvent.

The water employed to prepare the aqueous lysing reagent is preferably sufficiently deionized that it has a resistance greater than one megohm per centimeter. The lysing reagent may contain additives such as surfactants and the like. After admixing the components to form the lysing reagent, the lysing reagent may be filtered to remove any solid particles which may result from, e.g., dust or contaminants, undissolved impurities in the components, incomplete solution of one or more components, and the like. The filter may have a pore size less than about one, preferably about 0.1 to 0.5, micron. Frequently, however, filtration is unnecessary if the reagent is relatively free from undissolved impurities. The lysing reagent may be stored in any suitable container, e.g., glass or plastic, sealed containers.

An example of a lysing reagent in accordance with my invention is as follows with the specific example hereafter being referred to as lysing reagent L:

| Component | Amount per liter | |
|---|---|---|
| | Preferred | Specific |
| Sodium potassium tartrate | 5 to 50 grams | 19 grams |
| Cetyltrimethyl ammonium bromide | 10 to 50 grams | 15 grams |
| Denatured ethanol (Formula SDA-3A) | 5 to 100 milliliters | 20 milliliters |
| Water | to make one liter | |

The sodium potassium tartrate is technical grade, and the water has a resistance of greater than one megohm per centimeter. The lysing reagent is suitable for use with diluted blood samples. The diluent may be a blood diluent in accordance with my invention although other conventional, isotonic blood diluents which are not adverse to the formation of hemoglobin chromogens with the quaternary ammonium salt may alternatively be employed. The ratio of blood diluent to lysing reagent may, for instance, be about 5:1 to 20:1, e.g., about 8:1 to 10:1, and in Coulter scanning devices the final dilution of the blood is about 250 parts by volume total diluent and lysing agent per part by volume of a blood sample. The reactivity of the lysing reagent is observed to be essentially unchanged after storage for one year.

The blood diluent L and lysing reagent L hereabove described are used for blood analyses in a Coulter Model S scanning device obtainable from Coulter Electronics, Inc. A 44.7 microliter blood sample is admixed with 10 milliliters of blood diluent L. One milliliter of the mixture is drawn off and a 44.7 microliter portion of the mixture is obtained and further diluted with 10 milliliters of the blood diluent L. This diluted sample is analyzed for erythrocyte count and volume by electronic resistance measurements of the sample passing through an orifice. To the 9 milliliters of the first diluted blood sample is added one milliliter of the lysing reagent L, and the lysing of the erythrocytes is virtually instantaneous. Large particles or fragments resulting from the stromatolysing of erythrocytes are not observed in amounts which adversely affect the leukocyte determinations. The hemoglobin content is determined spectrophotometrically at the standard wave length of about $525 \pm 25$ nanometers, and the leukocyte count and volume is determined by electronic resistance measurements. The reagent permits the determinations to be conducted in the scanning device within 20 seconds of the addition of the reagent. From these direct measurements, the mean corpuscular hemoglobin concentration can be determined. The procedure is repeated for 200 samples and each sample is analyzed in three different Coulter Model S scanning devices. The results are compared with results obtained using conventional azide-containing blood diluent (Isotonic Diluent S blood diluent obtainable from Central Laboratories of Associated Maryland Pathologists, Ltd., Timonium, Maryland) and conventional ferricyanide-containing lysing agent (Lysing Agent S also obtainable from Central Laboratories of Associated Maryland Pathologists, Ltd.). The Coulter Model S scanning devices used in analyzing all the samples are calibrated by standard methods with respect to the conventional reagents, and no alteration in calibration is made when the scanning devices are employed using the blood diluent L and lysing reagent L. The results are provided in Table I.

TABLE I

| | Mean Values | | |
|---|---|---|---|
| Measurement | Blood diluent L Lysing reagent L | Comparative reagents | Generally Acceptable Deviation, % |
| White blood cell count ($\times 10^3$) | 8.82 | 8.97 | $\pm 7$ |
| red blood cell count ($\times 10^6$) | 4.182 | 4.155 | $\pm 6$ |
| hemoglobin (grams per deciliter) | 12.14 | 12.35 | $\pm 3.8$ |
| mean corpuscular volume (femtoliters) | 88.23 | 87.99 | $\pm 2.3$ |
| mean corpuscular hemoglobin concentration (%) | 32.63 | 33.77 | $\pm 2.9$ |

The variation in duplicate runs for the analyses employing the blood diluent L and lysing reagent L of the invention are compared to the variation in duplicate runs employing the conventional diluent and lysing agent. The comparison is made by calculating the ratio of standard deviation of the duplicates to the mean measurement value times 100 (coefficient of variation). Table II illustrates the calculated results wherein the lower the coefficient of variation for a given test, the more precise the measurement.

TABLE II

| Measurement | Coefficient of Variation | |
|---|---|---|
| | Blood diluent L Lysing reagent L | Comparative reagents |
| White blood cell count | 2.67 | 5.44 |
| Red blood cell count | 1.67 | 1.43 |
| Hemoglobin | 1.11 | 0.93 |
| Mean corpuscular volume | 0.68 | 0.66 |
| Mean corpuscular hemoglobin concentration | 0.92 | 1.58 |

It is claimed:

1. A lysing reagent for lysing erythrocytes while leukocytes remain substantially intact and forming chromogens with hemoglobin comprising a cyanide ion-free aqueous solution containing a minor amount sufficient for erythrocytolysis and forming chromogens with hemoglobin of a water-soluble quaternary ammonium salt of the formula $$R_1N(R_2)_3X$$

wherein $R_1$ is an alkyl having about 12 to 20 carbon atoms, each $R_2$ is the same or different and is lower alkyl or lower hydroxyalkyl, and X is an anion; and a minor amount sufficient to inhibit leukocytolysis of a water-soluble polycarboxylic acid, or salt thereof, of up to about 8 carbon atoms.

2. The lysing reagent of claim 1 wherein the quaternary ammonium salt is selected from the group consisting of a halide, sulfate, phosphate, or a nitrate salt.

3. The lysing reagent of claim 2 wherein the polycarboxylic acid or salt is a hydroxy-containing polycarboxylic acid or salt.

4. The lysing reagent of claim 3 wherein the polycarboxylic salt is an alkali metal salt.

5. The lysing reagent of claim 3 wherein in the quaternary ammonium salt, $R_1$ has about 14 to 18 carbon atoms and $R_2$ is alkyl of 1 to 3 carbon atoms.

6. The lysing reagent of claim 3 wherein the reagent further comprises a minor amount of lower alkanol.

7. The lysing agent of claim 6 wherein the polycarboxylic acid salt is sodium potassium tartrate.

8. The lysing reagent of claim 7 wherein the quaternary ammonium salt is cetyltrimethyl ammonium bromide.

9. The lysing reagent of claim 7 wherein in the quaternary ammonium salt, $R_1$ has about 14 to 18 carbon atoms and $R_2$ is alkyl of 1 to about 3 carbon atoms.

10. The lysing reagent of claim 9 comprising about 10 to 50 grams per liter cetyltrimethyl ammonium bromide; about 5 to 50 grams per liter sodium potassium tartrate; and about 5 to 100 milliliters of ethanol per liter of lysing reagent.

11. The lysing reagent of claim 10 wherein the quaternary ammonium salt is cetyltrimethyl ammonium bromide.

12. In a method for lysing erythrocytes and forming chromogens with hemoglobin while leukocytes remain substantially intact wherein a reagent is reacted with a blood sample for erythrocytolysis and for forming chromogens with hemoglobin, the improvement employing as the lysing reagent the lysing reagent of claim 1.

13. The method of claim 12 wherein the polycarboxylic salt comprises an alkali metal salt.

14. The method of claim 13 wherein in the quaternary ammonium salt, $R_1$ has about 14 to 18 carbon atoms and $R_2$ is alkyl of 1 to 3 carbon atoms.

15. The method of claim 12 wherein the quaternary ammonium salt is selected from the group consisting of a halide, sulfate, phosphate, or a nitrate salt.

16. The method of claim 15 wherein in the quaternary ammonium salt, $R_1$ has about 14 to 18 carbon atoms and $R_2$ is alkyl of 1 to 3 carbon atoms.

17. The method of claim 15 wherein the polycarboxylic acid or salt is a hydroxy-containing polycarboxylic acid or salt.

18. The method of claim 17 wherein the polycarboxylic salt is sodium potassium tartrate.

19. The method of claim 18 comprising about 10 to 50 grams per liter cetyltrimethyl ammonium bromide; about 5 to 50 grams per liter sodium potassium tartrate; and about 5 to 100 milliliters of ethanol per liter of lysing reagent.

20. The method of claim 15 wherein the reagent further comprises a minor amount of lower alkanol.

21. The method of claim 20 wherein the quaternary ammonium salt is cetyltrimethyl ammonium bromide.

22. The method of claim 21 wherein the quaternary ammonium salt is cetyltrimethyl ammonium bromide.

* * * * *